United States Patent [19]

Mutzhas

[11] 4,200,360
[45] Apr. 29, 1980

[54] FILTER FOR PROTECTION AGAINST RADIATION, ESPECIALLY WITH REGARD TO DIRECT PIGMENTATION BY SOLAR RADIATION

[76] Inventor: Maxim F. Mutzhas, Pilgersheimerstrasse 64, BRD 8000 Munich 90, Fed. Rep. of Germany

[21] Appl. No.: 776,518

[22] Filed: Mar. 11, 1977

Related U.S. Application Data

[63] Continuation-in-part of Ser. No. 773,844, Mar. 3, 1977.

[30] Foreign Application Priority Data

Mar. 5, 1976 [DE] Fed. Rep. of Germany ....... 2609273

[51] Int. Cl.² .............................................. G02B 5/20
[52] U.S. Cl. .................................... 350/316; 128/372; 252/300; 350/1.6; 350/311
[58] Field of Search .............. 350/1.6, 1.7, 311, 316, 350/321; 356/51; 252/300 G, 300 IR, 300 UV; 128/371, 372, 373, 374, 375, 396; 250/504

[56] References Cited

U.S. PATENT DOCUMENTS

| | | | |
|---|---|---|---|
| 2,444,976 | 7/1948 | Brown | 350/1.6 |
| 2,964,427 | 12/1960 | Rheinberger et al. | 350/1.6 X |
| 3,104,176 | 9/1963 | Hovey | 350/311 X |
| 3,112,490 | 12/1963 | Malcom, Jr. | 350/316 X |
| 3,126,295 | 3/1964 | Young | 252/300 G X |
| 3,269,267 | 8/1966 | Collins | 350/1.6 |
| 3,298,959 | 1/1967 | Marks et al. | 252/300 IR |
| 3,398,040 | 8/1968 | Allen et al. | 350/1.7 X |
| 3,483,871 | 12/1969 | Wilson | 128/372 |
| 3,718,533 | 2/1973 | Shibata | 350/1.6 X |
| 4,095,113 | 6/1978 | Wolff | 250/504 X |

FOREIGN PATENT DOCUMENTS

| | | | |
|---|---|---|---|
| 2335423 | 1/1975 | Fed. Rep. of Germany | 250/504 |
| 2457572 | 6/1975 | Fed. Rep. of Germany | 252/300 G |
| 551474 | 2/1943 | United Kingdom | 350/1.7 |

OTHER PUBLICATIONS

Gibson et al., "The Ultra-violet and Visible Transmission of Various Colored Glasses," *Tech. Papers of Bur. of Stand.*, Mar. 1920.

Alexander, "Absorption Filter Selection: How To", *Optical Spectra*, vol. 9, No. 8, Aug. 1975, pp. 29-33.

*Primary Examiner*—F. L. Evans
*Assistant Examiner*—John D. Lee
*Attorney, Agent, or Firm*—Allegretti, Newitt, Witcoff & McAndrews

[57] ABSTRACT

A radiation shield for promoting direct pigmentation of human skin by solar radiation comprising a filter made from a plurality of layers of synthetic plastic, e.g., polyester or inorganic glass, each filtering different ranges of wave lengths. Substantially all wave lengths below 320 nm and above 450 nm are filtered out so that rapid tanning of the skin is effected without burning.

12 Claims, 3 Drawing Figures

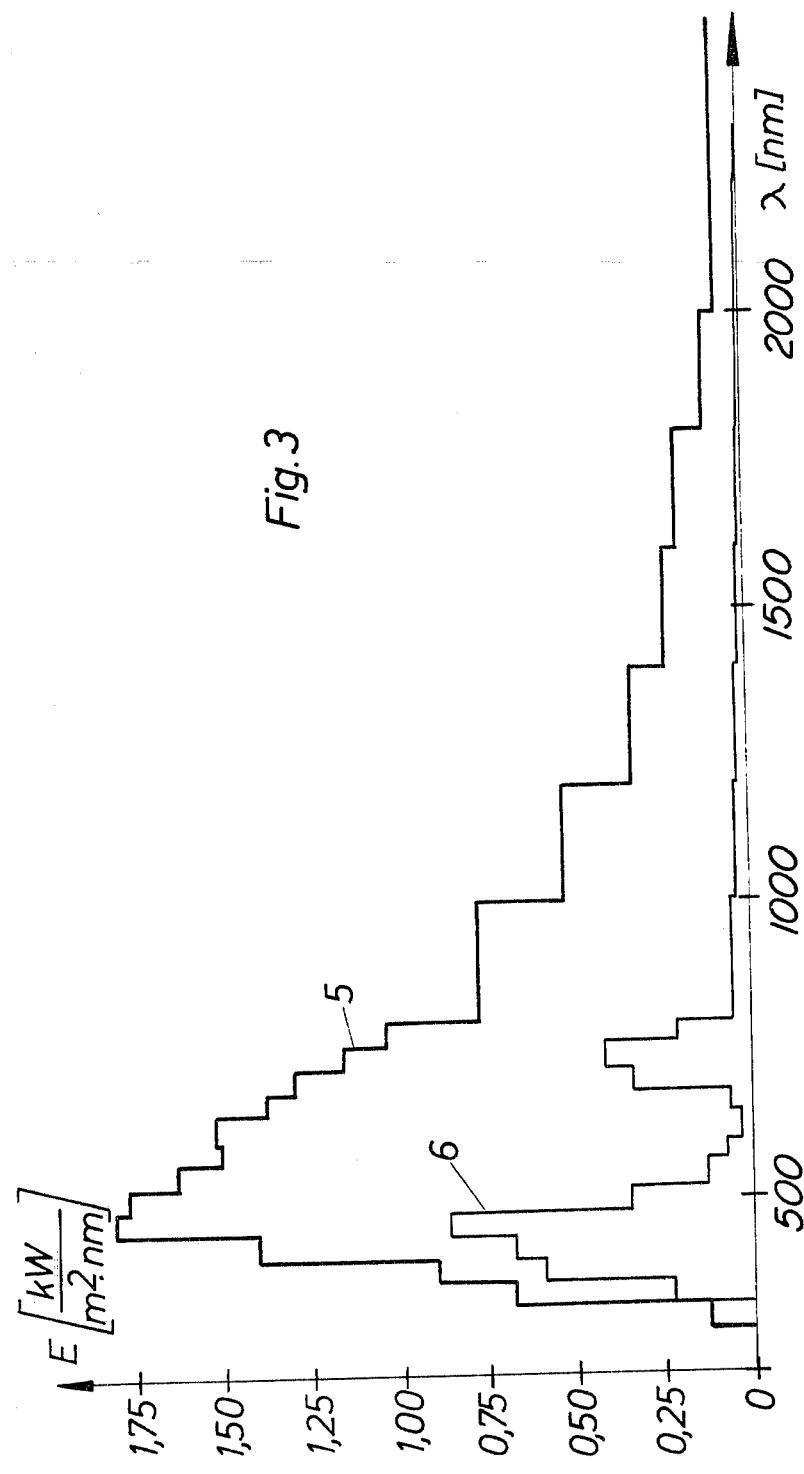

FILTER FOR PROTECTION AGAINST RADIATION, ESPECIALLY WITH REGARD TO DIRECT PIGMENTATION BY SOLAR RADIATION

This application is a continuation-in-part of application Ser. No. 773,844, filed Mar. 3, 1977.

The invention relates to a filter for protection against radiation, in particular with respect to direct pigmentation from solar radiation, although useful in connection with other sources of radiation.

For medical reasons it is necessary to expose the skin of the human body temporarily to natural radiation from the sun, in order to maintain important bodily functions for the sake of one's health. The pigmentation-ensuing influence of particular spectral ranges, results not only in a pleasantly tanned appearance corresponding to the contemporary cosmetic fashion, but this pigmentation also serves the purpose of protecting the otherwise unprotected skin from harmful radiations.

For example, the depositing of pigment in the skin protects extensively against erythema-producing rays, whose wave length is shorter than 320 nm. It has been known from the prior art that to protect the skin of the human body against sunburn, which is generated by wave lengths shorter than 320 nm, it is helpful to coat the body with suntan oil, lotion or cream. These cosmetics function to reduce extensively the harmful radiation effects which can lead to erythema. With the utilization of such agents for protection against the sun, the concept of a protective factor was introduced which indicates how long a time will lapse before human skin, coated with these means of protection against the sun, reaches the point of an erythema.

This factor is measured by the erythema-swelling time of the uncoated skin. In the case of sun oil the factor of solar protection lies in the order of magnitude of 2, in the case of the customary sun lotions, in the order of magnitude of 4. Higher values up to about 10 are to be attained with sun-cream.

All these cosmetic filtering preparations, however, cannot assure absolute protection against the formation of erythema (sunburn), since they do not filter out completely the radiations below 320 nm. Insofar as this is possible however, they also let through so little radiation effective for tanning (above 320 nm) that while there is little danger of sunburn, direct tanning is extensively avoided. In this connection a positive role is also played by the fact that various skin types do not tolerate particular solar protection means and the ultraviolet absorber contained in them, so that these persons are obliged to withdraw extensively from the wholesome influence of sunshine.

When the surface of the skin is coated with sun-protection agents, one cannot assume with certainty that the thicknesses of the layers are absolutely uniform and that every part of the body which is exposed to radiation is protected. Thus, the sun-protection substances, which are known and available on the market, offer no absolutely reliable protection against the harmful effects of radiation upon the human skin. In this regard it is not only sunburn but also the carcinogenous effects that must be taken into consideration. Furthermore, these cosmetic substances, which for the most part cannot be brought in contact with the mucous membrane and/or the eye, fail to protect the eye against rays, which below 320 nm, can lead to inflammation of the cornea, i.e., photokeratitis. Particularly in high mountain ranges and occasionally also at sea level, exposure can lead to inflammation of the conjunctiva, provoked by radiation in the order of magnitude of 300 nm. Conjunctiva generally takes a very painful course.

Hitherto no synthetics were known which have a higher range of transmission in the ultraviolet than in the visible light range, or the close/near infra-red range, which extends between about 800 nm and 2000 nm. Furthermore, no synthetics are known which, in the range of the "close infra-red", have a lower degree of transmission than in the corresponding range of visible light.

The basic object of the invention is to create a radiation-protective filter, which makes it possible in the case of solar radiation, to tan directly in a quick, pleasant and physiologically safe manner, and whereby all harmful or dangerous radiation components are safely filtered out.

This object is achieved according to the invention by interposing a filter, made of solid material, between the sun and the body to be irradiated which blocks all physiologically harmful radiations, that is, short waves lower than 320 nm, and transmits radiation in the range most effective for direct tanning, that is, from 320 nm to 450 nm.

In order to protect a body to be highly irradiated from excessive heat load, in accordance with another feature of the invention, the range of radiation above 450 nm, is filtered out as far as possible through materials which block in the visible and the infra red range.

In further embodiment of the invention the solid body filter consists of several layers spatially separated from one another, whereby each layer in different spectral ranges becomes effective in combination to produce optimal transmission for direct tanning, while screening the harmful and troublesome radiation particles. This solid body filter can be constructed either of inorganic glass or of organic synthetic material.

Useful inorganic glasses include silicate glasses or quartz. The organic synthetic materials include polyacrylic glass, polyesters or similar resins.

In one construction of the solid body filter, the carrier material (inorganic glass and/or synthetic), is provided with a coating of absorption or reflection layers, which are either vacuum-evaporated or applied as substrata. The coating may also be applied by transferring, spraying or spreading. An additional possibility consists of fusing to sinter on these absorption or reflection layers as coating layers on the carrier material.

An additional embodiment of the invention envisages that the layers, preferably applied by vacuum evaporation as substrata, function as interference layers. This means that the thicknesses of the layers lie in the range of the wave lengths of the corresponding radiation. In this connection, layers consisting of thorium oxide, titanium oxide and indium oxide prove to be particularly favorable.

An additional embodiment of the invention envisages that the absorbing materials are dissolved in solid body filters, and preferably distributed colloidally fine. In the utilization of inorganic glass for UV-light and/or IR-absorbers, metal oxides and also elemental metals must be colloidally distributed. In the case of synthetics it is feasible to incorporate absorbers for the individual spectral ranges.

Instead of the organic absorbers finely-ground particles of the blue-violet filter glass, preferably silicate glass, or heat-absorption glass containing an organic ultraviolet absorber, can be dispersed in the synthetic in order to attain the desired filter effect.

These synthetic filter materials can also be ground up, sprayed on or stamped on a carrier material such as for example acrylic glass or polyester.

In order to be able to produce economically quality filters from inorganic glass, ground inorganic absorption glass may be incorporated into synthetic material in which case care must be exercised that the refraction index of the synthetic material to which the glass powder is added does not differ too greatly from that of the inorganic glass powder. In order to achieve an intimate dispersion between the organic synthetic material and the inorganic glass powder, it is desirable to coat the glass powder beforehand with an adhesive such as, for example, silicon finish, preferably in fluid solution. In this connection mixtures of alcohol, acetic acid and water have proved satisfactory as carrier fluid for the silicon finish. In this way filters can be produced economically in all desired forms, e.g., in block, plate or foil form for all customary optical or physiological purposes. They may be used to replace highly expensive inorganic glass filters which are difficult to manufacture. For low-cost production of these organic filters, glass as well as the residues from glass melts can be utilized.

Particularly in the case of ultraviolet filters which possess a higher degree of transmission than those which operate in the visible range, a blue-tinting of the transmitted sunlight occurs. This blue-tinting can on the one hand be perceived psychologically positive, as cool. On the other hand this tinting can be a disadvantage for particular applications. For such applications, where white light must be transmitted, complementary color pigments may be incorporated to correct the color position to give the impression that the transmitted light is white (color mixing). In this manner practically any desired color position can be produced, even that that leads to radiation of yellow-reddish color, in order to attain a psychologically acceptable warm light.

The previously mentioned adhesive base, e.g., silicon finish, can also be applied to the surface of the carrier material to be coated, in order to attain a particularly intimate adherence between filter layer and carrier material.

The latter purpose can also be attained if the granulated glass is adhered to the organic material, in which case it has proved feasible to coat the side of the filter coated with granulate, with a white layer of organic material, preferably by varnishing or lining with foil. In the latter case, instead of hot pressing the embedding material over self-adhering material, transfer adhesives can be used.

An additional method for producing such filters is by preparing fibers from the corresponding organic or inorganic filter glasses, then to adhere these to the filter in a suitable mixture by braiding or weaving them. By mixing various filter fibers, practically all desired spectral transmission degree curves can be produced.

It is also possible to evaporate the inorganic filter glasses, to deposit by sedimentation or to adhere in sheets to the inorganic carrier material. The advantages attained with the invention may be summarized as follows:

Because of the fact that the wave lengths below 320 nm are absorbed, the danger of sunburn is almost entirely eliminated, so that this radiation arrangement has a solar protection factor of infinity. During radiation periods of any desired length, no sunburn occurs. At the same time the arrangement does not reduce the direct tanning of the unprotected skin. Thus, the human skin tans rapidly and safely without the danger of sunburn. Furthermore, filtering out radiation below 320 nm eliminates those wave lengths which, according to current scientific knowledge can lead to skin cancer. All carcinogenic radiation ranges are completely filtered out. Furthermore, the danger of conjunctivitis or photokeratitis, as well as the peril of the formation of cataracts (these are irreversible, producing clouding of the lens of the eye) is excluded, since all these maladies, according to the present level of science, originate from radiation of short wave length, less than 320 nm.

On a cloudless day with sun inclination at 90°, the intensity of the solar and global radiation together amounts to about 1120 W/m$^2$ at the earth's surface. Of this total radiation intensity about 1 W/m$^2$ radiation is effective for erythema, while 52 W/m$^2$ radiation is effective for direct pigmentation (with reference to the pigmentation maximum at about 340 nm). If it is assumed that the erythemic threshold dose has a value of 250 Ws/m$^2$ (again with reference to the maximum sensitivity to erythema), taking this as a basis, the result is that the unprotected human skin will have attained the erythema threshold after about four minutes exposure under the conditions mentioned.

The threshold index for direct pigmentation amounts to about 100,000 Ws/m$^2$ (with reference to the pigmentation maximum) so that the unprotected human body skin, after about 30 minutes, can attain the pigmentation threshold. From this it is apparent that for the unprotected body skin the threshold period for direct pigmentation is about 8 times higher than the threshold period for the formation of erythema.

Even with the application of an extremely effective sun protection agent having a solar protection factor of 10, the erythema formation occurs after 40 minutes, i.e., after 40 minutes the skin would already have received sufficiently harmful radiation to be definitely sunburned. Also because the sun protection agent filters out a large part of the radiation effecting direct pigmentation, the swelling time for attaining the threshold of pigmentation is increased substantially. This means that the erythema will set in before the sun-tanning.

If on the other hand radiation below 320 nm is filtered out for example through a polyester sheet 0.175 mm in thickness, then the solar protection factor rises to the value of infinity, since no erythema-inducing radiation is allowed to penetrate. The threshold of pigmentation is reached in less than one hour. The total radiation load reaching the body in this case is reduced somewhat in contrast to the unfiltered radiation and amounts to about 950 W/m$^2$.

The considerable heat load of 1120 W/m$^2$, imposed upon the human body under the previously-described conditions, is also present with the use of the most extreme cosmetic solar protection agents. This value cannot be reduced by these agents. In order to diminish it, it is necessary to bring special filters between sun and the body to be irradiated, in order to screen the sun's rays in the range above 450 nm (which are not necessary for direct sun-tanning).

Thus for example, in the utilization of a filter combination of heat absorbing glass 4 mm in thickness, a polyester sheet with a thickness of 0.175 mm, and a blue-violet glass of 1 mm in thickness, filtering in the visible range, the following may be accomplished: The erythema threshold will approach infinity, since no radiations lower than 320 nm penetrate. The direct pigmentation threshold is reached after about one hour of radiation time under the conditions previously described, while the radiation charge striking the entire body has dropped to about 130 W. Through this filter combination it is assured that 100 percent of the radiation harmful to the human body under 320 nm, is filtered out, while about 60 percent of the radiation effective for the direct sun-tanning will pass through the filter combination. On the other hand 94 percent of the radiation lying above 450 nm, basically leading only to heat loading is filtered out. The filter combination insures that even if no scatterlight could penetrate laterally, the intensity of illumination still lies in the order of magnitude of about 1000 Lux, so that activities such as reading, working and the like can be performed. The invention will subsequently be explained more fully with specific embodiments with the aid of the drawing.

In the drawing

FIG. 3 shows the spectral energy distribution of unfiltered and filtered sunlight ($E=f(\lambda)$).

Figure 1:
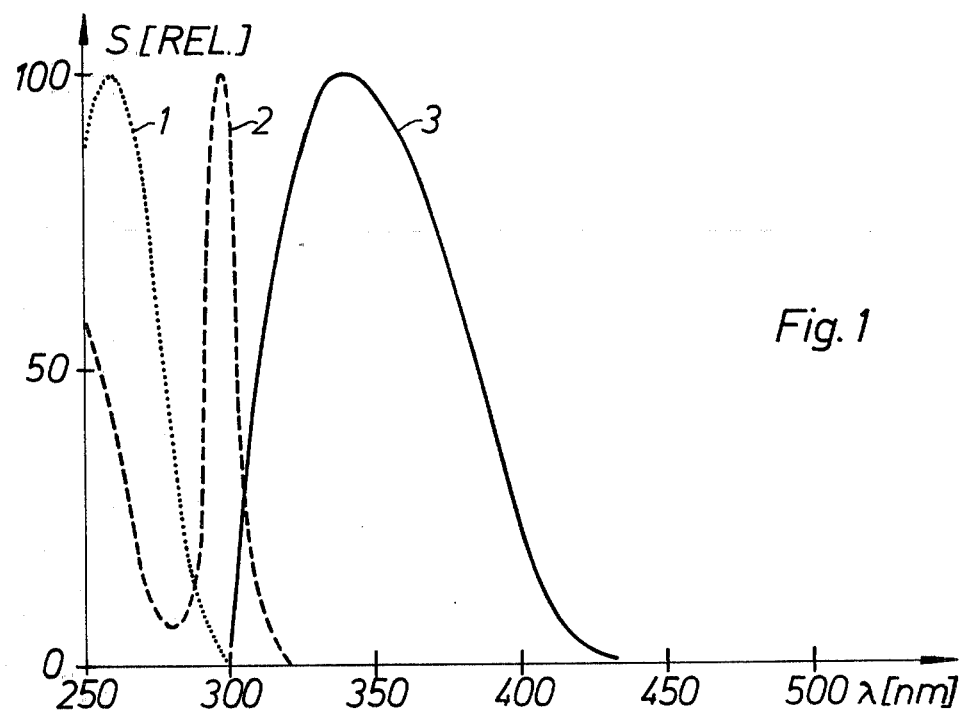
FIG. 1 shows the spectral sensitivity curves, for conjunctivitis, erythema and direct sun tanning ($s=f(\lambda)$).
Figure 2:
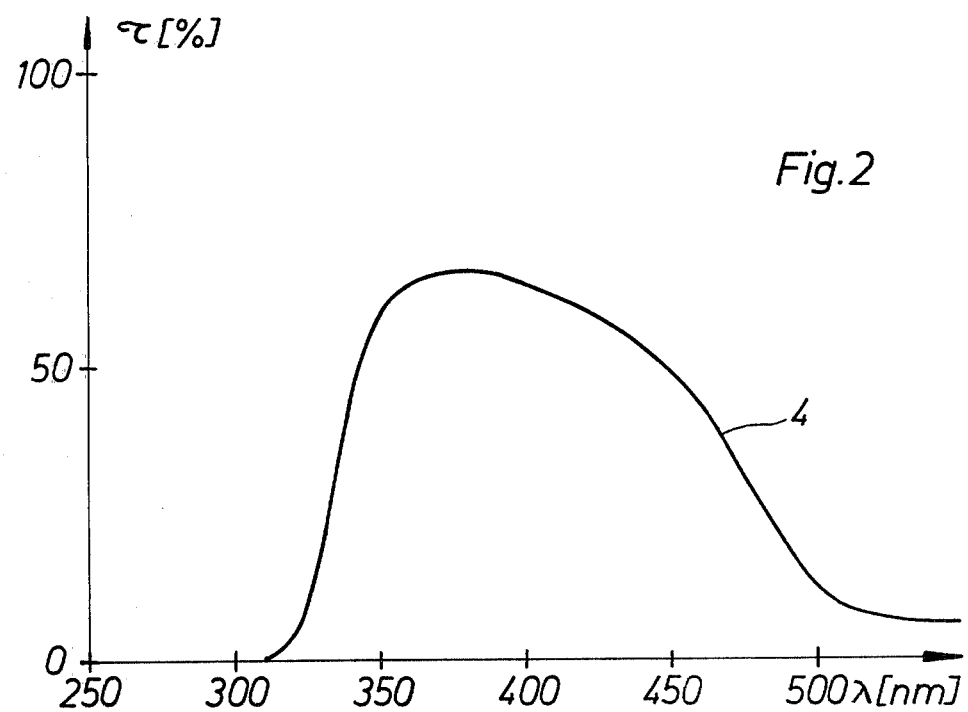
FIG. 2 shows the transmission degree curves of the filter combination ($\tau=f(\lambda)$).

FIG. 1 shows the relative conjunctivitis-sensitivity curve 1, the relative erythema sensitivity curve 2 and the relative curve of effectiveness for direct sun tanning 3, conditioned by the wave length of the emitted radiation. FIG. 2 shows the transmission degree of the filter as a function of the wave length. Represented is the curve 4 of the filter combination, consisting of an ultraviolet filter (the wave lengths below 320 nm filtered out); blue-violet filter (the light above 440 nm extensively filtered out); and the infra-red filter (which filters out about 94 percent of the total infra-red range). FIG. 3 shows the total radiation strength (intensity) 5 of the solar radiation at a 90° elevation of the sun with a cloudless sky as well as the portion of the solar radiation 6 which passes the filter. Also the outside limit of 320 nm for the harmful radiation is drawn in.

Applications for this invention include sun-shield tents, sun-shield screens, sun-shield frames, protective films in the form of hoods or hangings, wearing apparel or bathing suits, roofing for sunterraces, reclining devices, reclining areas, roof coverings for worksites and residences. In all applications the radiation which promotes health is allowed to penetrate with the cosmetic effect of the direct pigmentation, while the heat load and the UV-load are virtually excluded.

The direct pigmentation can be accelerated and strengthened by external or internal application of methyoxypsorals. For external use a solution of 0.75 to 1.5% of 8 MOP is suitable.

This radiation shield filter finds application in conjunction with the methoxypsoral for the treatment of psoriasis, hyperbilirubinemia, or similar ailments.

The invention is also useful for polymerization and synthetic resin and varnish drying, especially if in these procedures excessively strong radiation loads in the spectral ranges above 450 nm are to be prevented.

This radiation shield filter may also be used to filter artificial sources of rays.

Thus, for all these purposes, the organic carrier material in combination with granular inorganic filter glass provides a reasonably priced optical filter for any desired spectral ranges. The carrier material may be injection molded or extruded at much lower cost than conventional inorganic glass filters.

What I claim is:

1. A radiation shield for promoting direct pigmentation of human skin by solar radiation comprising a solid translucent material including finely ground inorganic filter glass particles, which filter glass normally and also when included as said particles in combination with said solid translucent material filters out all wave lengths shorter than 320 nm, blocks wave lengths over 450 nm and which permits maximum transmission of wave lengths in the range of 320 to 450 nm.

2. The shield of claim 1 in which said solid translucent material comprises a plurality of spatially-separated layers, each effective to filter a different range of wave lengths.

3. The shield of claim 1 in which said solid translucent material is made of synthetic organic material.

4. The shield of claim 3 wherein said solid material is coated with absorption layers and reflection layers.

5. The shield of claim 4 in which said layers contain complementary color pigments to correct the coloring position.

6. The shield of claim 3 including wave-length-absorbing material comprising glass granules pressed into the surface of said solid translucent material, the latter being a synthetic organic resin.

7. The shield of claim 6 in which said granules are coated with an additional layer of inorganic filtering material.

8. The shield of claim 3 in which wave length absorbing material is distributed throughout said solid translucent material as colloidal size particles.

9. The shield of claim 8 in which said wave-length-absorbing material consists of ground blue-violet glass incorporated in synthetic organic material.

10. The shield of claim 1 in which said solid translucent material is synthetic organic material containing finely ground inorganic glass particles coated with an adhesive to promote intimate mixing with the organic material.

11. The shield of claim 10 in which said adhesive is deposited from a carrier comprising alcohol, acetic acid and water.

12. The shield of claim 10 in which said adhesive is a silicon finish.

* * * * *